(12) United States Patent
Williams et al.

(10) Patent No.: US 9,962,515 B2
(45) Date of Patent: May 8, 2018

(54) VENTILATOR EXHALATION FLOW VALVE

(71) Applicant: CareFusion 303, Inc., San Diego, CA (US)

(72) Inventors: Malcolm R. Williams, San Clemente, CA (US); Adrian D. DeSilva, Riverside, CA (US); Huy Thanh Vu, Westminster, CA (US)

(73) Assignee: CAREFUSION 303, INC., San Diego, CA (US)

( * ) Notice: Subject to any disclaimer, the term of this patent is extended or adjusted under 35 U.S.C. 154(b) by 41 days.

(21) Appl. No.: 15/233,853

(22) Filed: Aug. 10, 2016

(65) Prior Publication Data

US 2016/0346499 A1 Dec. 1, 2016

Related U.S. Application Data

(62) Division of application No. 13/931,418, filed on Jun. 28, 2013, now Pat. No. 9,433,743.

(51) Int. Cl.
*A61M 16/20* (2006.01)
*A61M 16/00* (2006.01)
(Continued)

(52) U.S. Cl.
CPC ...... *A61M 16/205* (2014.02); *A61M 16/0003* (2014.02); *A61M 16/0051* (2013.01);
(Continued)

(58) Field of Classification Search
CPC .. A61M 16/205; A61M 16/024; A61M 16/04; A61M 16/06; A61M 16/0875; A61M 16/0066; A61M 16/204; A61M 16/0057; A61M 16/0051; A61M 16/0003; A61M 2205/3331; A61M 2205/581; A61M 2205/505; A61M 2205/3317; A61M 2205/128; A61M 2205/125;
(Continued)

(56) References Cited

U.S. PATENT DOCUMENTS

| 2,037,880 A | 4/1936 | Charavay |
|---|---|---|
| 2,510,125 A | 6/1950 | Meakin |

(Continued)

FOREIGN PATENT DOCUMENTS

| EP | 0829793 A1 | 3/1998 |
|---|---|---|
| EP | 1127583 A2 | 8/2001 |

(Continued)

OTHER PUBLICATIONS

International Search Report and Written Opinion for Application No. PCT/US2015/038155, dated Dec. 17, 2015, 18 pages.
(Continued)

*Primary Examiner* — Ian Paquette
(74) *Attorney, Agent, or Firm* — McDermott Will & Emery LLP

(57) ABSTRACT

Described herein is an exhalation valve for a ventilator that controls gas flow through a patient exhalation line in response to a target pressure within the line. The valve controls gas flow by (i) providing both a high frequency signal and a low frequency signal through a coil positioned in a fixed magnetic field, (ii) determining a position of the coil by detecting the high frequency signal, and (iii) controlling a position of the coil by adjusting the low frequency signal.

9 Claims, 6 Drawing Sheets

(51) Int. Cl.
*F16K 31/06* (2006.01)
*A61M 16/04* (2006.01)
*A61M 16/06* (2006.01)
*A61M 16/08* (2006.01)

(52) U.S. Cl.
CPC .... *A61M 16/0057* (2013.01); *A61M 16/0066* (2013.01); *A61M 16/024* (2017.08); *A61M 16/04* (2013.01); *A61M 16/06* (2013.01); *A61M 16/0875* (2013.01); *A61M 16/204* (2014.02); *F16K 31/0675* (2013.01); *F16K 31/0679* (2013.01); *A61M 2016/003* (2013.01); *A61M 2016/0027* (2013.01); *A61M 2016/0039* (2013.01); *A61M 2016/0042* (2013.01); *A61M 2205/125* (2013.01); *A61M 2205/128* (2013.01); *A61M 2205/3317* (2013.01); *A61M 2205/3331* (2013.01); *A61M 2205/505* (2013.01); *A61M 2205/581* (2013.01)

(58) Field of Classification Search
CPC .. A61M 2016/0042; A61M 2016/0039; A61M 2016/0027; A61M 2016/003; F16K 31/0679; F16K 31/0675
See application file for complete search history.

(56) References Cited

U.S. PATENT DOCUMENTS

| | | | |
|---|---|---|---|
| 2,634,311 | A | 4/1953 | Darling |
| 3,140,042 | A | 7/1964 | Fujii |
| 3,673,541 | A | 6/1972 | Volinskie |
| 3,776,215 | A | 12/1973 | Howard et al. |
| 3,788,765 | A | 1/1974 | Rusak |
| 4,243,357 | A | 1/1981 | Flynn et al. |
| 4,543,041 | A | 9/1985 | French et al. |
| 4,562,744 | A | 1/1986 | Hall et al. |
| 4,571,801 | A | 2/1986 | Ewing |
| 4,754,651 | A | 7/1988 | Shortridge et al. |
| 4,809,742 | A | 3/1989 | Grau |
| 4,825,904 | A | 5/1989 | Grau et al. |
| 4,909,545 | A | 3/1990 | Hohol |
| 4,978,281 | A | 12/1990 | Conger, IV |
| 5,064,346 | A | 11/1991 | Atarashi et al. |
| 5,127,400 | A | 7/1992 | DeVries et al. |
| 5,207,239 | A | 5/1993 | Schwitalla |
| 5,265,594 | A | 11/1993 | Olsson et al. |
| 5,277,196 | A | 1/1994 | Hankinson et al. |
| 5,295,397 | A | 3/1994 | Hall et al. |
| 5,331,995 | A | 7/1994 | Westfall et al. |
| 5,339,807 | A | 8/1994 | Carter |
| 5,365,795 | A | 11/1994 | Brower, Jr. |
| 5,461,932 | A | 10/1995 | Hall et al. |
| 5,478,206 | A | 12/1995 | Prahst |
| 5,537,992 | A | 7/1996 | Bjoernstijerna et al. |
| 5,572,992 | A | 11/1996 | Kankkunen et al. |
| 5,604,681 | A | 2/1997 | Koeninger |
| 5,606,236 | A | 2/1997 | Tennies et al. |
| 5,771,884 | A | 6/1998 | Yarnall et al. |
| 5,918,596 | A | 7/1999 | Heinonen |
| 5,954,051 | A | 9/1999 | Heinonen et al. |
| 6,151,557 | A | 11/2000 | Braden et al. |
| 6,422,092 | B1 | 7/2002 | Morrison et al. |
| 6,553,923 | B2 | 4/2003 | Gatley, Jr. |
| 6,578,818 | B1 | 6/2003 | Krimmer et al. |
| 6,609,431 | B1 | 8/2003 | Tietsworth et al. |
| 6,622,724 | B1 | 9/2003 | Truitt et al. |
| 6,820,620 | B2 | 11/2004 | Rochat |
| 6,945,123 | B1 | 9/2005 | Kuehl et al. |
| 8,504,318 | B2 | 8/2013 | Mendelson et al. |
| 2002/0085952 | A1 | 7/2002 | Ellingboe et al. |
| 2002/0198668 | A1 | 12/2002 | Lull et al. |
| 2003/0106554 | A1 | 6/2003 | de Silva et al. |
| 2003/0220605 | A1 | 11/2003 | Bowman et al. |
| 2004/0074311 | A1 | 4/2004 | Lull et al. |
| 2004/0177703 | A1 | 9/2004 | Schumacher et al. |
| 2005/0004534 | A1 | 1/2005 | Lockwood et al. |
| 2006/0144163 | A1 | 7/2006 | Friberg |
| 2006/0162466 | A1 | 7/2006 | Wargo et al. |
| 2006/0236781 | A1 | 10/2006 | Ohmi et al. |
| 2007/0193369 | A1 | 8/2007 | Evans et al. |
| 2007/0265877 | A1 | 11/2007 | Rice et al. |
| 2007/0277824 | A1 | 12/2007 | Aylsworth et al. |
| 2008/0059084 | A1 | 3/2008 | Wang et al. |
| 2008/0092891 | A1 | 4/2008 | Cewers |
| 2009/0038615 | A1 | 2/2009 | Bradley |
| 2009/0093774 | A1 | 4/2009 | Wang et al. |
| 2009/0113996 | A1 | 5/2009 | Wang et al. |
| 2009/0293634 | A1 | 12/2009 | Ong |
| 2009/0326839 | A1 | 12/2009 | Rogers et al. |
| 2010/0139660 | A1 | 6/2010 | Adahan |
| 2010/0229967 | A1 | 9/2010 | Yasuda et al. |
| 2010/0236552 | A1 | 9/2010 | Kwok et al. |
| 2010/0307490 | A1 | 12/2010 | Broborg et al. |
| 2011/0100364 | A1 | 5/2011 | Faram |
| 2011/0126834 | A1 | 6/2011 | Winter et al. |
| 2012/0185102 | A1 | 7/2012 | Skoglund et al. |
| 2012/0204874 | A1 | 8/2012 | Sofranko |
| 2012/0226449 | A1 | 9/2012 | Delache et al. |
| 2012/0229272 | A1 | 9/2012 | Jacob et al. |
| 2012/0285454 | A1 | 11/2012 | Nibu et al. |
| 2012/0318383 | A1 | 12/2012 | Yasuda et al. |
| 2013/0079667 | A1 | 3/2013 | Berkcan et al. |
| 2013/0220314 | A1 | 8/2013 | Bottom |
| 2013/0247905 | A1 | 9/2013 | Miller et al. |
| 2014/0054479 | A1 | 2/2014 | Shen |
| 2014/0066880 | A1 | 3/2014 | Prince et al. |
| 2014/0182590 | A1 | 7/2014 | Platt et al. |
| 2014/0251322 | A1 | 9/2014 | Miller |
| 2014/0326242 | A1 | 11/2014 | Ahmad et al. |
| 2015/0096560 | A1 | 4/2015 | Klenner et al. |
| 2015/0143921 | A1 | 5/2015 | Postberg et al. |

FOREIGN PATENT DOCUMENTS

| | | |
|---|---|---|
| EP | 2402616 A1 | 1/2012 |
| JP | S56597 A | 1/1981 |
| WO | WO-0138832 A2 | 5/2001 |
| WO | WO-2006024532 A1 | 3/2006 |
| WO | WO-2011055254 A1 | 5/2011 |
| WO | WO-2013002699 A1 | 1/2013 |
| WO | WO-2013080079 A1 | 6/2013 |

OTHER PUBLICATIONS

International Search Report and Written Opinion for Application No. PCT/US2015/038157, dated Nov. 5, 2015, 12 pages.
International Search Report and Written Opinion for international Application No. PCT/US2014/044737, dated May 19, 2015, 18 pages.
International Search Report and Written Opinion in PCT Application No. PCT/US2014/044438 dated Oct. 28, 2014, 11 pages.
International Search Report and Written Opinion in PCT Application No. PCT/US2014/044441 dated Oct. 31, 2014, 12 pages.
International Search Report and Written Opinion in PCT Application No. PCT/US2014/044442 dated Nov. 3, 2014, 10 pages.
International Search Report and Written Opinion in PCT Application No. PCT/US2014/044724 dated Oct. 21, 2014, 12 pages.
International Search Report for International Application No. PCT/US2014/044743, dated Jan. 22, 2015, 6 pages.
Invitation to Pay Additional Fees and Partial Search Report for Application No. PCT/US2015/038155, dated Oct. 7, 2015, 7 pages.
Invitation to Pay Additional Fees in International Application No. PCT/US2014/044737 dated Oct. 28, 2014, 7 pages.
Invitation to Pay Additional Fees in PCT Application No. PCT/US2014/044743 dated Oct. 21, 2014, 7 pages.
Fehr, R., "The Basics of Inductance", Feb. 1, 2003, EC&M.
Australian Examination Report No. 1 for Application No. 2014302094, dated Feb. 14, 2018, 3 pages.

VENTILATOR EXHALATION FLOW VALVE

CROSS-REFERENCES TO RELATED APPLICATIONS

This application is a divisional of pending U.S. patent application Ser. No. 13/931,418, filed Jun. 28, 2013, entitled "Ventilator Exhalation Flow Valve," which is herein incorporated by reference in its entirety.

BACKGROUND

Field

The present disclosure generally relates to ventilation systems and, in particular, to a ventilator flow valve.

Description of the Related Art

Patients with respiratory injury, such as chronic respiratory failure, may be provided with a ventilator to assist with their breathing or, in severe cases, take over the breathing function entirely. Ventilators typically provide a flow of air, or other breathing gases, at an elevated pressure during an inhalation interval, followed by an exhalation interval where the pressurized air is diverted so that the air within the patient's lungs can be naturally expelled. The inhalation interval may be initiated upon detection of a patient's natural inhalation or by the ventilator.

Ventilators are available in a variety of sizes with different ranges of air flows and pressures that can be provided. For example, a neonatal patient will require a much lower pressure and volume of air per breath than an adult.

SUMMARY

Described herein is a ventilator having an exhalation valve that is a software-controlled valve used to adjust the flow of gas passing through an expiratory port of the ventilator to the outside environment. The exhalation valve is controlled by a software control signal and works in conjunction with a ventilator's gas delivery subsystems to maintain user set pressure control levels. In exhalation, and in continuous positive airway pressure ("CPAP") therapy, the exhalation valve preferably maintains a set pressure, and outlet flow is controlled at a specified target bias flow rate. Additional (demand) flow is provided to maintain the pressure in the event of patient inspiratory flow exceeding the bias flow.

Some embodiments described herein relate to a valve that includes a valve orifice with an adjustable opening; a fixed magnetic field; a force coil configured to be moved within the fixed magnetic field in response to a low frequency current; a current amplifier configured to direct a summed low frequency current and a high frequency current into the force coil; a feedback coil configured to detect the high frequency current in the force coil, the detected high frequency current having a magnitude that is proportional to a force coil position within the fixed magnetic field. The valve can also include a processor configured (i) to receive data relating to the position of the force coil and (ii) to send instructions to the current amplifier; and a diaphragm configured to adjust the valve orifice opening based on the position of the force coil.

Described herein are ventilator systems that include, for example, a gas source configured to provide a gas to a patient via a supply channel; an exhaust channel configured to direct exhaust gas from the patient; and an exhaust valve. The exhaust valve may include a force coil configured to be moved within a fixed magnetic field in response to a low frequency current; a current amplifier configured to direct a summed low frequency current and a high frequency current into the force coil; a feedback coil configured to detect the high frequency current in the force coil; a processor configured (i) to receive data relating to the position of the force coil, (ii) to receive data relating to pressure within the exhaust channel, and (iii) to send instructions to the current amplifier based on the position of the coil and the pressure; and a diaphragm configured to adjust opening of a valve orifice based on the instructions from the processor.

Described herein are also methods for adjusting pressure in a ventilator line. Some methods include the following steps: directing a summed low frequency current and a high frequency current from a current amplifier into a force coil that is configured (i) to be moved within a fixed magnetic field in response to the low frequency current and (ii) to control a diaphragm to adjust opening of a valve orifice; detecting the high frequency current in the force coil, the detected high frequency current having a magnitude that is proportional to a position of the force coil within the fixed magnetic field; detecting the pressure in the ventilator line; and changing the low frequency current to move the force coil within the fixed magnetic field, thereby adjusting the opening of a valve orifice, in response to the detected pressure.

For purposes of summarizing the disclosure, certain aspects, advantages, and novel features of the disclosure have been described. It is to be understood that not necessarily all such advantages may be achieved in accordance with any particular embodiment of the disclosure. Thus, the disclosure may be embodied or carried out in a manner that achieves or optimizes one advantage or group of advantages as taught herein without necessarily achieving other advantages taught or suggested.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
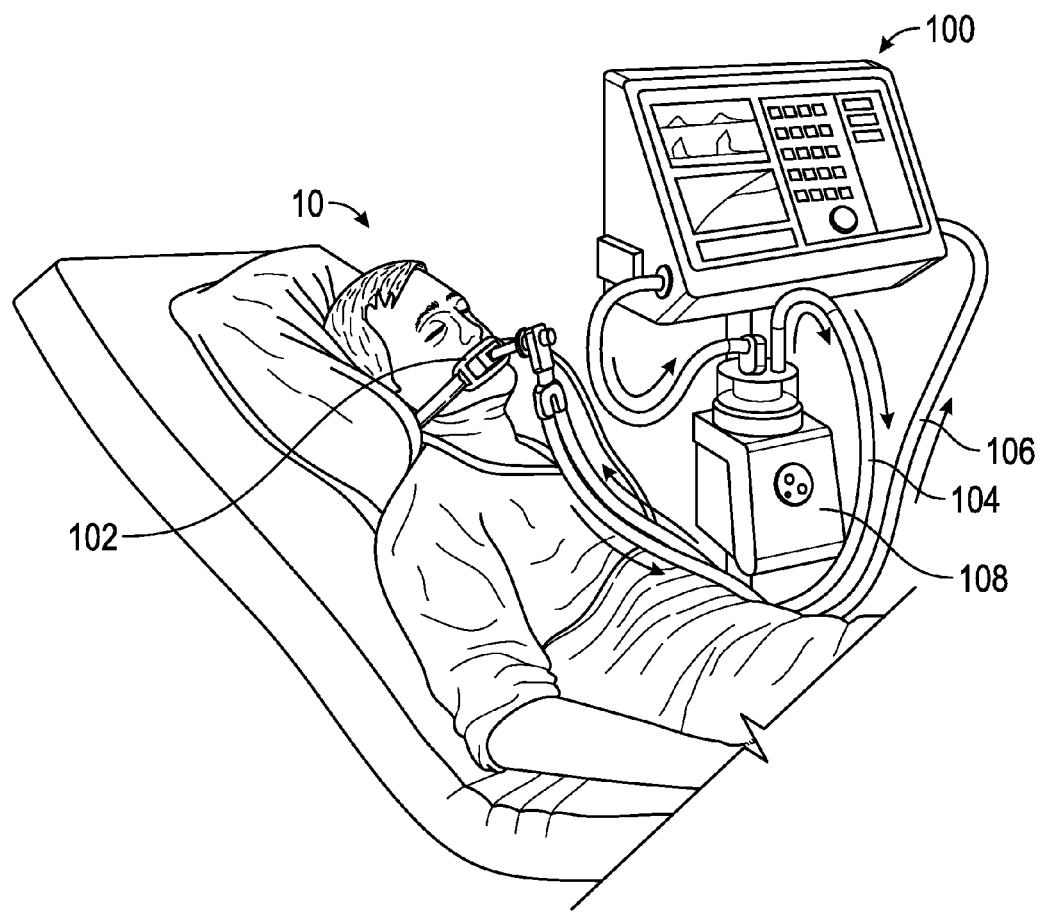
FIG. 1 depicts a patient using an exemplary ventilation system according to certain aspects of the present disclosure.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the discussion herein is directed to a ventilator for use in a hospital, the disclosed concepts and methods may be applied to environments, such as a home or long-term care facility, and other fields, such as deep-sea diving, that would benefit from accurate flow measurement of a variety of gas mixtures. Those of skill in the art will recognize that these same features and aspects may also be applied to the sensing and control of other fluids besides medical gases.

Within this document, the term "gas" shall be interpreted to mean both a single material in gaseous form, for example oxygen, and a mixture of two or more gases, for example air or heliox (a mixture of oxygen and helium). A gas may include water or other liquids in the form of vapor or suspended droplets. A gas may also include solid particulates suspended in the gas.

Within this document, the term "pure," when used with reference to a gas, means that the gas meets commonly accepted medical standards for purity and content.

Within this document, the term "temperature sensor" means a device configured to measure temperature and to provide a signal that is related to the measured temperature. A temperature sensor may include electronics to provide a drive current or voltage and/or measure a current or voltage. The electronics may further include conditioning and conversion circuitry and/or a processor to convert the measured value to a signal that may be in analog or digital form.

Within this document, the term "pressure sensor" means a device configured to measure a gas pressure and provide a signal that is related to the measured pressure. A pressure sensor may include electronics to provide a drive current or voltage and/or measure a current or voltage. The electronics may further include conditioning and conversion circuitry and/or a processor to convert the measured value to a signal that may be in analog or digital form. The pressure may be provided in absolute terms or "gauge" pressure, i.e., relative to ambient atmospheric pressure.

An exhalation subsystem of a ventilator comprises an exhalation valve, an exhalation flow sensor, and a heated filter and water trap. As explained herein, the exhalation valve is a software-controlled valve that is used to adjust the flow of gas passing through the expiratory port of the ventilator to the outside environment. The exhalation valve is controlled by a software control signal and works in conjunction with a ventilator's gas delivery subsystems to maintain user set pressure control levels.

As explained herein, the exhalation valve operates on the principle of a force balance across a control diaphragm, which is preferably a disposable valve membrane. In some embodiments, a linear magneto-mechanical actuator controls a force on the diaphragm, which in turn controls the circuit or ventilator line pressure. The force generated by the actuator is based on a command from the software closed-loop controller.

FIG. 1 depicts a patient 10 using an exemplary ventilation system with a ventilator 100 according to certain aspects of the present disclosure. The ventilator 100 operates as a gas source for providing gas to a patient (e.g., for respiration). In this example, the ventilator system includes a supply channel, tube, or "limb" 104, a return or exhaust channel, tube, or limb 106, a conditioning module 108 that may, for example, warm or humidify the air passing through the supply limb 104. The supply and exhaust limbs 104, 106 are both coupled to a patient interface device 102 that, in this example, is a mask that fits over the mouth of the patient 10. In other embodiments (not shown in FIG. 1), the patient interface device 102 may include a nasal mask, an intubation device, or any other breathing interface device as known to those of skill in the art.

Figure 2A:
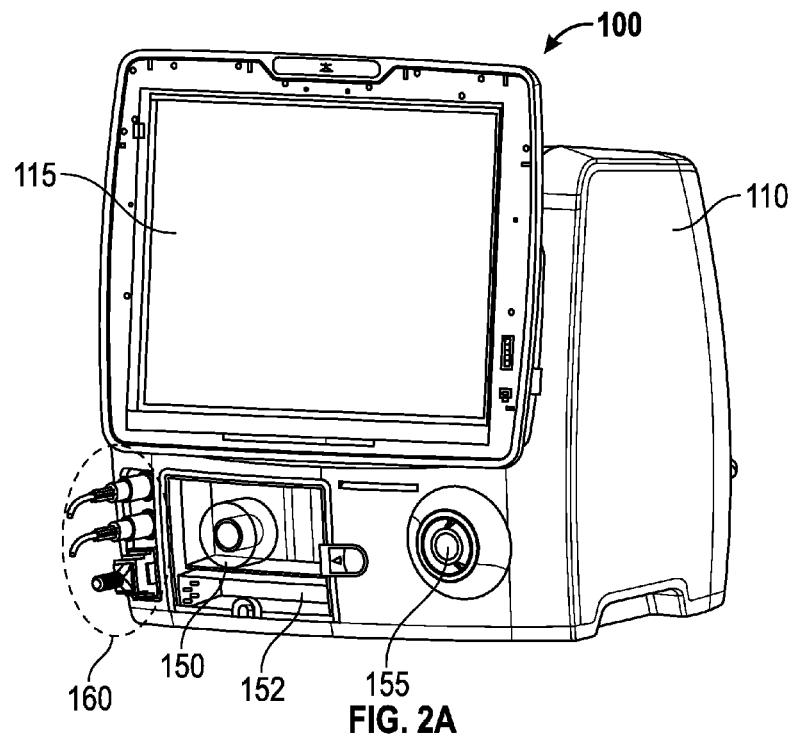
FIGS. 2A and 2B are front and rear views of an exemplary ventilator according to certain aspects of the present disclosure.
Figure 2B:
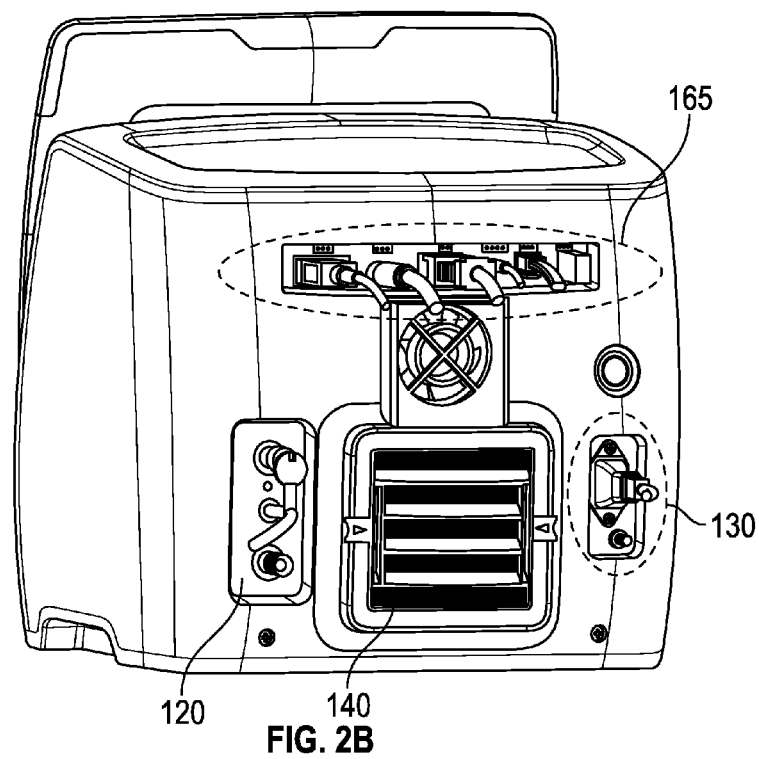

FIGS. 2A and 2B are front and rear views of the ventilator 100 according to certain aspects of the present disclosure. The ventilator 100 has a housing 110 with an attached user interface 115 that, in certain embodiments, comprises a display and a touchscreen. In FIG. 2A, it can be seen that the front of the housing 110 includes a supply port 155 for a supply limb, such as supply limb 104 in FIG. 1, and a return port 150 for an exhaust, such as exhaust limb 106 in FIG. 1. The return port 150 may be mounted over an access door 152 that provides access to a filter (not visible in FIG. 2A) that filters and absorbs moisture from the exhaled breath of the patient 10. In certain embodiments, there may also be a front connection panel 160 for connection to external instruments or a network interface cable.

FIG. 2B shows a rear view of the ventilator 100 with a gas inlet adapter 120, an air intake port 140, and a power interface 130 that may include a power plug connector and a circuit breaker reset switch. There may also be a rear interface panel 165 for connection to external instruments or a network interface cable.

Figure 3:
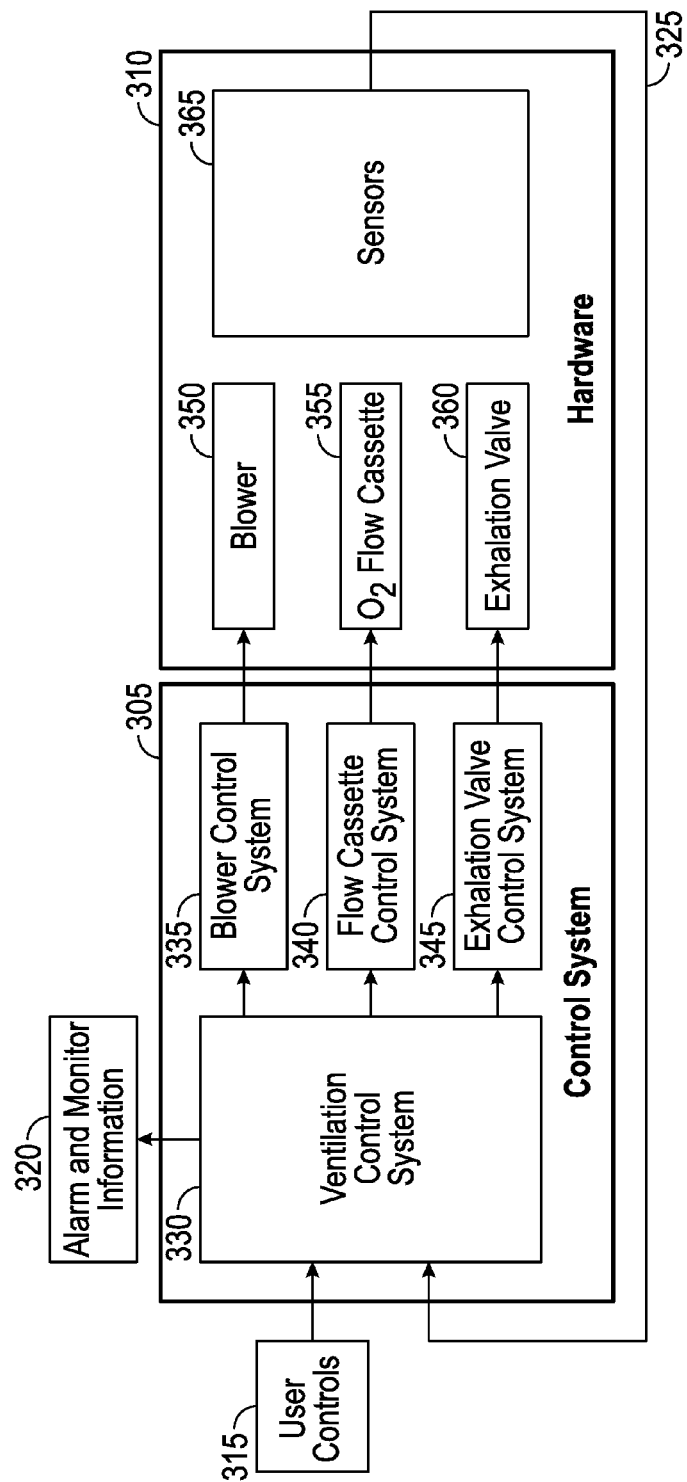
FIG. 3 is a schematic representation of a ventilator according to certain aspects of the present disclosure.

FIG. 3 illustrates a schematic depiction of the ventilator 100 having a control system 305, system hardware 310, user input 315, output 320, and feedback 325. The control system 305 includes a ventilation control system 330 that receives user input 315. The control system 305 includes hardware control systems that control respective hardware components of the ventilator 100. For example, the hardware control systems may include a blower control system 335, a flow cassette control system 340, and an exhalation valve control system 345. The blower control system 335 controls a respective blower 350, the flow cassette control system 340 controls a respective flow cassette 355, and the exhalation valve control system 345 controls a respective exhalation valve 360.

The system hardware 310 includes sensors 365 that detect information from the system hardware 310, for example, the blower 350, the flow cassette 355, and the exhalation valve 360. The sensors 365 produce one or more feedback signals 325 that are received by the ventilation control system 330. The ventilation control system 330 receives the feedback control signals 325 and the user input 315 and sends information to an output 320. The output 320 can include, for example, monitoring information and alarms.

Figure 4:
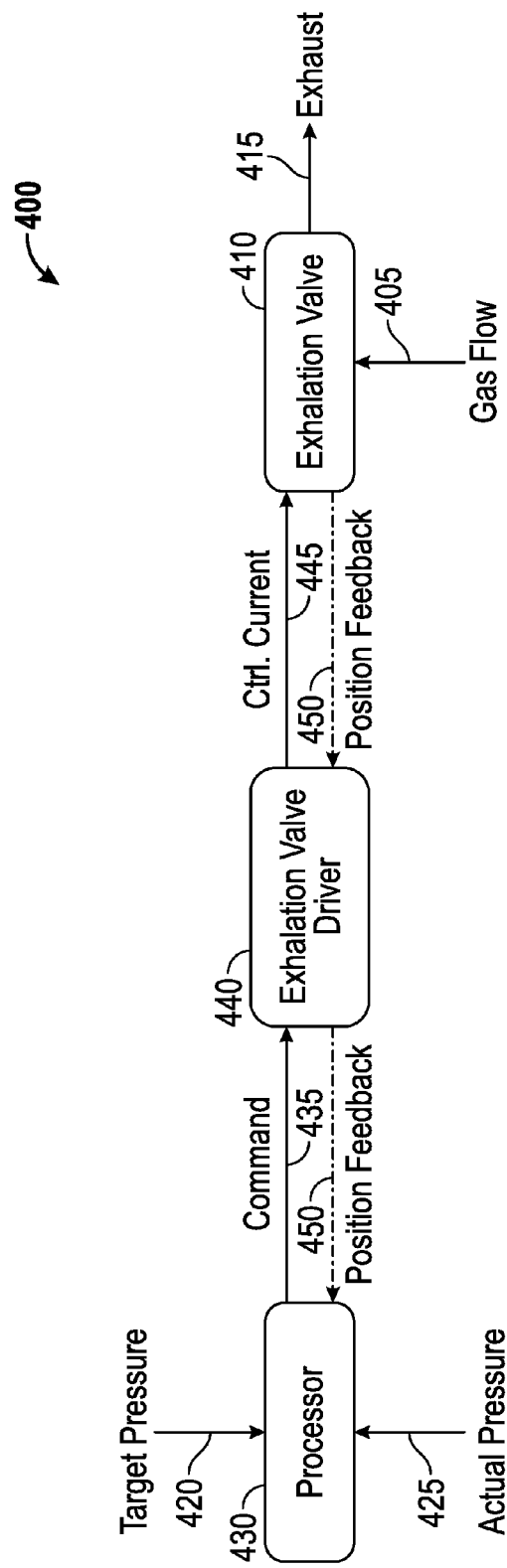
FIG. 4 is a schematic depiction of a feedback system according to certain aspects of the present disclosure.

One example of feedback and control of the ventilator 100 is depicted in FIG. 4, which illustrates a schematic depiction of an exhalation control feedback system 400 that determines an amount of gas flow 405 that is permitted to pass through an exhalation valve 410. The illustrated embodiment of the feedback system 400 is based on a target pressure 420 and an actual circuit pressure 425 (or a pressure within a line of the ventilator 100).

As illustrated in FIG. 4, a processor 430 receives an input signal relating to the actual circuit pressure 425 and compares the actual circuit pressure 425 to the target pressure 420. Based on this comparison, the processor 430 sends a command signal 435 to an exhalation valve driver 440. The exhalation valve driver 440 is configured to control a position of the exhalation valve 410 to regulate the gas flow 405 through the exhalation valve 410. In the illustrated embodiment, the exhalation valve driver 440 sends a control current 445 to the exhalation valve 410 to maintain or adjust the exhalation valve 410 to modify or adjust the pressure within the ventilator line.

For example, if the actual circuit pressure 425 was found to be too high, the processor 430 sends a command 435 to the exhalation valve driver 440 to open the exhalation valve 410 to reduce pressure within the ventilator line. The exhalation valve driver 440, upon receiving the command 435 to relieve pressure, adjusts the control current 445 to the exhalation valve 410 to increase the opening of the exhalation valve 410 and relieve pressure within the ventilator line. As the control current 445 increases the opening of the exhalation valve 410, the processor 430 receives position feedback 450 of the exhalation valve 410 via the exhalation valve driver 440, such that the processor 430 is able to determine the degree to which the exhalation valve 410 is open.

If the actual circuit pressure 425 input to the processor 430 was found to be too low, the processor 430 directs the driver 440 to adjust the control current 445 to the exhalation valve 410 to decrease the opening of the exhalation valve 410 such that pressure within the ventilator line is increased. If the actual circuit pressure 425 input to the processor 430 was found to be at an acceptable level or within an acceptable range, the processor 430 directs the driver 440 to maintain the control current 445 to the exhalation valve 410 to maintain the position of the exhalation valve 410.

Figure 5:
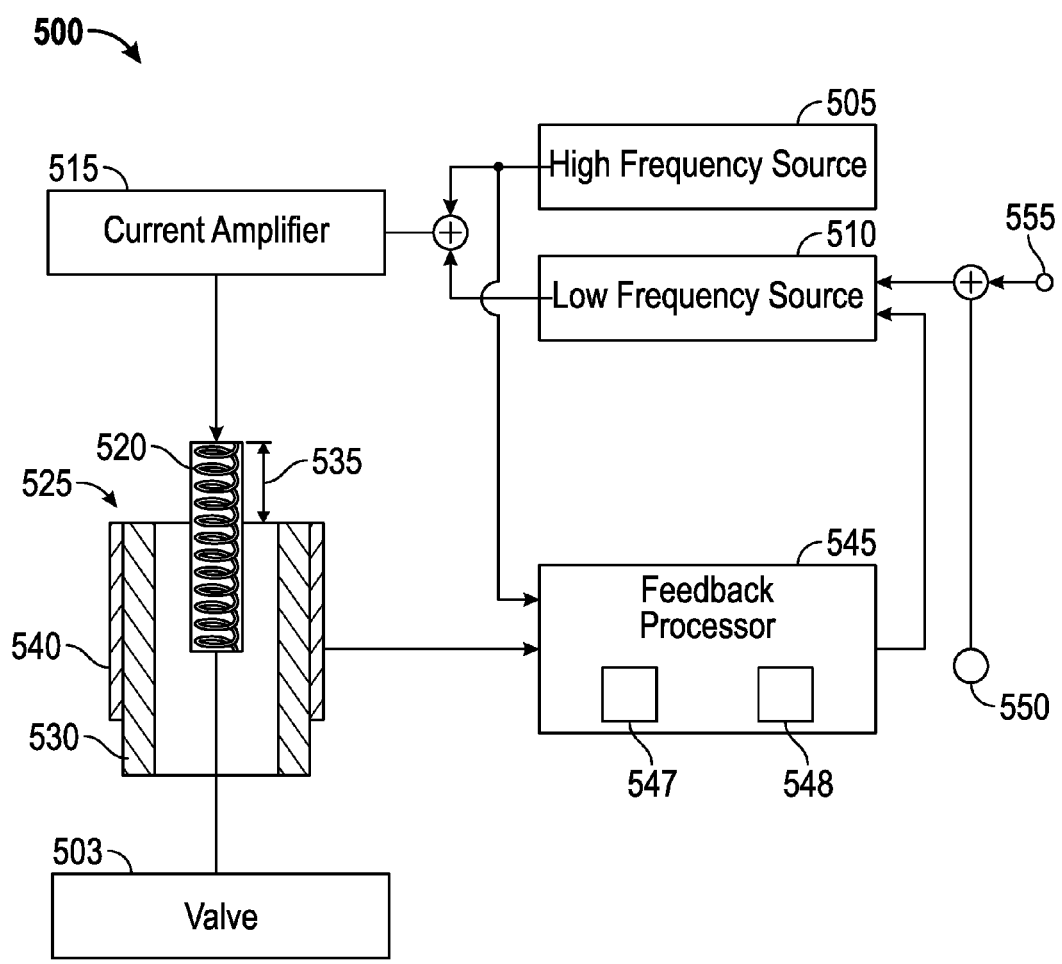
FIG. 5 illustrates an exemplary schematic arrangement of a control system according to certain aspects of the present disclosure.

FIG. 5 illustrates an exemplary schematic arrangement of a current control system 500 that illustrates some embodiments of a driver (e.g., the exhalation valve driver 440 of FIG. 4) operating to adjust a valve 503 (e.g., the exhalation valve 410). In the illustrated system 500, a high frequency source 505 generates a signal having a high frequency, and a low frequency source 510 generates a signal having a low frequency. The high frequency signal and the low frequency signal are summed together, and the signal is amplified by a current amplifier 515. In some embodiments, the current amplifier 515 is a linear current output amplifier. The signal is then directed to a coil 520 (e.g., a force coil) that is configured to move at least partly within a fixed magnetic field 525. The fixed magnetic field 525 is produced by a magnetic field generator, e.g., at least one permanent magnet 530 or a separate coil (not shown).

The natural frequency of the coil 520 is such that the coil 520 responds to the low frequency component of the combined signal by movement within or in relation to the magnetic field, as illustrated by arrows 535. In some embodiments, the low frequency component is less than about 90% of the natural frequency of the coil 520. In some embodiments, the low frequency component is less than about 80% of the natural frequency of the coil 520, and in yet further embodiments, the low frequency component is less than about 50% of the natural frequency of the coil 520.

The high frequency component of the combined signal preferably has a negligible effect on the position of the coil 520 such that the position of the coil 520 within the magnetic field is controlled substantially by the low frequency component. For example, in some embodiments, the high frequency component is more than 50% greater than the natural frequency of the coil 520. In some embodiments, the high frequency component can be between 50% and about 200% greater than the natural frequency of the coil 520. In yet additional embodiments, the high frequency can be more than 200% greater than the natural frequency of the coil 520.

A detection coil 540, or a feedback coil, detects the high frequency component of the signal passing through the coil 520, and the detection coil 540 sends a signal to a high frequency feedback processor 545 that determines, based on the detection coil 540 signal, a position of the coil 520 within the magnetic field 525. In some embodiments, a magnitude of the high frequency signal detected by the detection coil 540 is used to determine the position of the coil 520 within the magnetic field 525. In some instances, the high frequency feedback processor 545 also determines a velocity of the coil 520 within the magnetic field 525 and the high frequency feedback processor 545 sends a signal to the low frequency source 510 for providing feedback on the position and/or velocity of the coil 520. In some embodiments, the high frequency feedback processor 545 includes a position circuit 547 and a velocity circuit 548.

The low frequency source 510 also receives input from a sensor (not shown) within a ventilator line relating to how actual pressure 550 within the ventilator line compares to a target pressure 555 of the ventilator line. Based on (i) the input relating to the comparison of actual pressure 550 and the target pressure 555 and (ii) the input from the high frequency feedback processor 545 relating to the position of the coil 520 in relation to the magnetic field 525, the low frequency source 510 determines whether the low frequency signal should be modified to change the position of the coil 520 in relation to the magnetic field 525.

For example, if the actual pressure 550 were determined to be outside of an acceptable range of pressures set by the target pressure 555, the low frequency source 510 changes the low frequency signal to move the coil 520 within the magnetic field 525. The coil 520 is preferably coupled, directly (e.g., mechanically) or indirectly (e.g., magnetically), to a portion of the valve 503 that regulates flow through the valve 503. Accordingly, movement of the coil 520 moves the portion of the valve 503 and changes an amount of gas passing through the valve 503. As the amount of gas passing through the valve 503 changes, the pressure within the ventilator line changes, and the actual pressure 550 is detected and compared with the target pressure 555.

In some embodiments, it is advantageous to maintain a positive pressure within the ventilator line. For example, when the ventilator line is an exhalation line, or exhalation pathway, from a patient, and it is desirable to maintain a positive pressure within the patient's lungs relative to a local atmospheric pressure (or ambient pressure), the target pressure 555 may include a minimum threshold pressure. When the actual pressure 550 is determined to drop below the threshold pressure, the low frequency source 510 may be configured to close the valve 503, such that substantially no gas from the exhalation line passes through the valve 503. The valve 503, in such instances, may remain closed until the actual pressure 550 within the exhalation line increases above the threshold pressure, at which time, the low frequency source 510 receives inputs reflecting that the valve 503 should be opened, and the source 510 changes the low frequency signal to move the coil 520 to a position in relation to the magnetic field 525 that corresponds to an opening of the valve 503. In some instances, upon receiving a signal that the actual pressure 550 is above the threshold pressure, the low frequency source 510 may produce a signal that maintains position of the coil 520, and therefore the valve 503, to further increase the actual pressure within the exhalation line.

Figure 6:
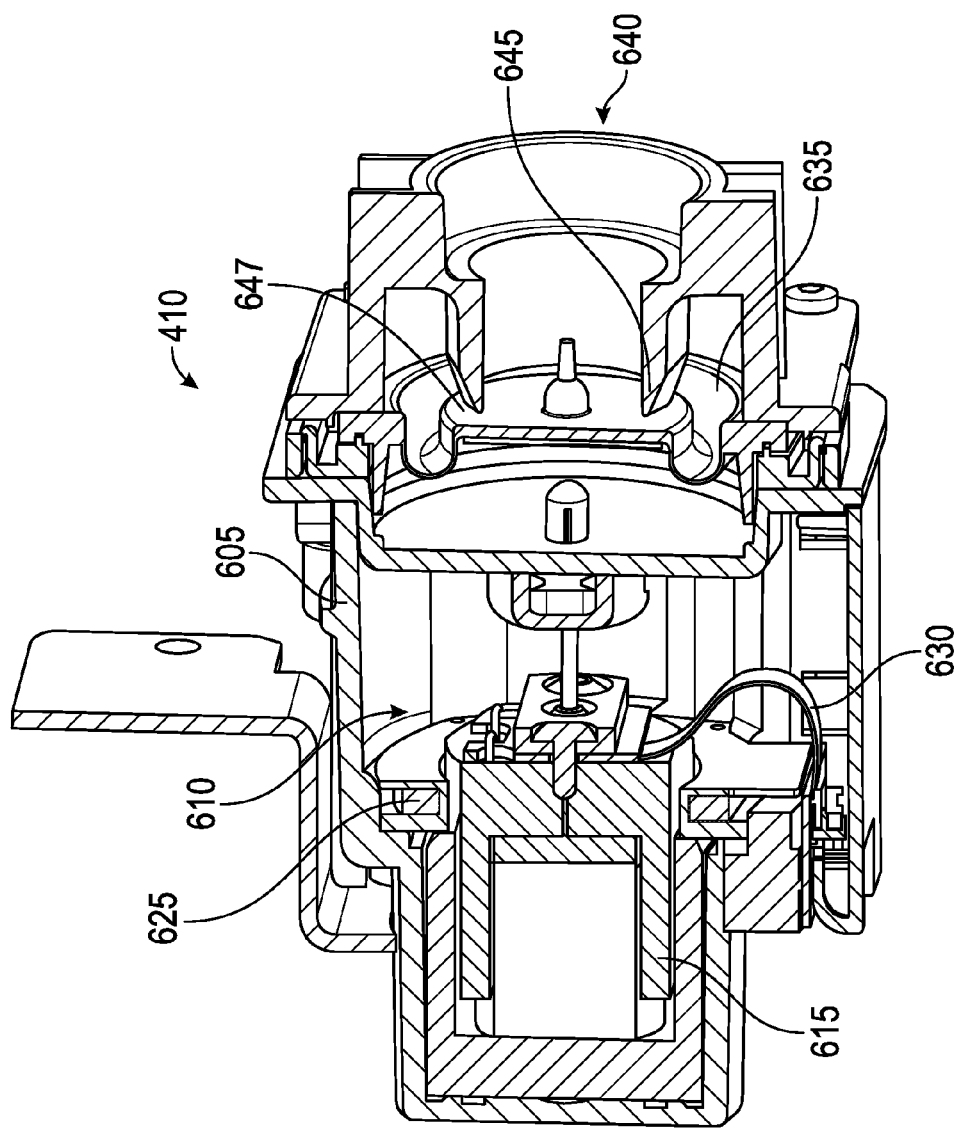
FIG. 6 is a cross sectional view of a flow valve according to certain aspects of the present disclosure.

FIG. 6 is an exemplary cross sectional view of the exhalation valve 410, which operates under the same or similar principles described above with respect to valve 503 depicted in FIG. 5. The illustrated exhalation valve 410 includes a housing 605 that defines an internal chamber 610. Disposed within the internal chamber 610 is a coil 615 that is positioned and axially movable within or in relation to a fixed magnetic field generator 620. Positioned about at least a portion of the magnetic field generator 620 is a sensor 625. In some embodiments, the sensor 625 is a detection coil that is configured to detect high frequency signals passing through the coil 615. The high frequency signals detected by the sensor 625 are used to determine a position of the coil 615 within or in relation to the magnetic field generator 620.

A signal is communicated from the sensor 625 regarding a position of the coil 615, and signals are directed to the coil 615 via a flexible communication cable 630. As the signals directed to the coil 615 cause the coil 615 to move within the internal chamber 610 in relation to the magnetic field, movement of the coil 615 affects positioning of a convoluted diaphragm 635 and poppet 647. The poppet 647 operates as a variable orifice of the valve 410. Positioning of the poppet 647 with respect to the seat 645 affects the amount of fluid that passes through a valve having an opening 640.

Movement of the coil 615 can change a position of the plunger 625 by being directly coupled to the poppet 647 and moving the poppet 647 toward or away from a seat 645, which defines the valve orifice as the gap between the poppet 647 and seat 645. In some embodiments, movement of the coil 615 can change a position of the poppet 647 by being indirectly coupled to the poppet 647. For example, a portion of the coil 615 and a portion of the poppet 647 may be magnetically opposed or attracted to each other. In such embodiments, movement of the coil 615 thereby opposes or attracts the portion of the poppet 647. In a similar configuration to direct coupling, this indirect coupling can affect positioning of the poppet 647 in connection with the seat 645 of the valve without contact between the coil 615 and the poppet 647.

Although a diaphragm with a poppet are illustrated in FIG. 6, other types of valve configurations may be used in connection with the described embodiments. For example, other valves that can be used include, but are not limited to, a flap valve, a rotating disk valve, a duck-billed valve, etc.

The exhalation valve 410 can also provide increased stability by damping the moving components of the exhalation valve 410. As explained above, a velocity of the coil 615 can be determined by a processor (e.g., processor 430 or high frequency feedback processor 545), which can include a velocity circuit that calculates a change of position with respect to time. The velocity can then be used to determine the desired damping. With the assumption that the valve 410 functions as a second order system, the damped frequency response is greater than or equal to about 26 Hz, and the damping coefficient that yields an under-damped or critically damped valve assembly. In other embodiments, additional damping such as pneumatic viscous damping can be incorporated into the valve 410 to further tune the valve 410 to the specific application.

The exhalation valve 410 can include a "fail-safe" open feature in case of loss of electrical power, software control, or loss of all inlet gases. The exhalation valve 410 can also be configured to switch to the "fail-safe" open configuration when the ventilator 100 is turned off. On successful completion of power on checks, the ventilator 100 will close the exhalation valve 410 and normal ventilation can commence. During a ventilator 100 "fail-safe" open condition, the exhalation valve 410, and other valves or ports will work in conjunction to (i) relieve pressure from the circuit down to ambient pressure conditions, (ii) allow ambient air to be available to the patient for breathing, and (iii) minimize re-breathing of gases.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A ventilator system comprising:
   a gas source configured to provide a gas to a patient via a supply channel;
   an exhaust channel configured to direct exhaust gas from the patient; and
   an exhaust valve comprising:
      a force coil configured to be moved within a fixed magnetic field in response to a low frequency current;
      a current amplifier configured to direct a summed current comprising a low frequency current and a high frequency current into the force coil;
      a feedback coil configured to detect the high frequency current in the force coil;
      a processor configured (i) to receive data relating to the position of the force coil, (ii) to receive data relating to pressure within the exhaust channel, and (iii) to send instructions to the current amplifier based on the position of the coil and the pressure; and
      a diaphragm configured to adjust opening of a valve orifice based on the instructions from the processor.

2. The system of claim 1, wherein the processor is configured to receive data relating to a velocity of the force coil and to direct a signal to the current amplifier to change the position of the force coil.

3. The system of claim 1, wherein the instructions are configured to adjust the position of the force coil by adjusting the low frequency current.

4. The system of claim 1, wherein the fixed magnetic field is generated by at least one permanent magnet.

5. The system of claim 1, wherein the processor is configured to direct the current amplifier to change the position of the force coil to close the valve orifice when a pressure within the exhaust channel falls below a threshold pressure.

6. The system of claim 5, wherein the threshold pressure is above an ambient pressure.

7. A method for adjusting pressure in a ventilator line, the method comprising:
   directing a summed current comprising a low frequency current and a high frequency current from a current amplifier into a force coil that is configured (i) to be moved within a fixed magnetic field in response to the low frequency current and (ii) to control a diaphragm to adjust opening of a valve orifice;
   detecting the high frequency current in the force coil, the detected high frequency current having a magnitude that is proportional to a position of the force coil within the fixed magnetic field;
   detecting the pressure in the ventilator line; and
   changing the low frequency current to move the force coil within the fixed magnetic field, thereby adjusting the opening of a valve orifice, in response to the detected pressure.

8. The method of claim 7, wherein the low frequency current is changed to close the valve orifice when the detected pressure drops below a threshold pressure.

9. The method of claim 8, wherein the threshold pressure is above an ambient pressure.

* * * * *